US00PP10314P

United States Patent [19]

Morren

[11] Patent Number: Plant 10,314

[45] Date of Patent: Apr. 7, 1998

[54] VARIETY OF APPLE TREE NAMED EXCEL

[75] Inventor: Jos Morren, Halen, Belgium

[73] Assignee: Jomobel NV, Belgium

[21] Appl. No.: 787,612

[22] Filed: Jan. 23, 1997

[30] Foreign Application Priority Data

Jan. 25, 1996 [EP] European Pat. Off. ..... 199/96

[51] Int. Cl.[6] ..... A01H 5/00

[52] U.S. Cl. ..... Plt./34.1

[58] Field of Search ..... Plt./34.1

*Primary Examiner*—James R. Feyrer

*Attorney, Agent, or Firm*—Olson & Olson

[57] ABSTRACT

A new and distinctive variety of apple *Malus domestica*, tree named Excel, a sport mutation of the apple variety Jonagold, uniquely characterized from its parent variety by its much better color intensity over 50% or more of the surface of the fruit with a solid bright red colored blush with scarcely visible very fine red stripes in it and a smoother texture of the skin surface. Also the ground color of its fruit keeps longer green. The fruit has a higher acidity and a longer and thinner brown/red stalk, and has earlier ripening and picking dates. The tree is also characterized by distinctly dormant fruit buds on tips which have a conical shape and by its dark brown-red wood with clearly more pubescence and fewer but bigger lenticels than its parent variety.

4 Drawing Sheets

This application claims the benefit of the right of priority accorded under the International Convention for the Protection of New Varieties of Plants (UPOV Convention) of European Union Community Plant Variety Rights Application NR 0199/96 filed 25 Jan. 1996.

BACKGROUND AND GENERAL STATEMENT OF THE INVENTION

This invention relates to a new and distinct variety of apple tree named Excel.

The new apple variety was discovered in a cultivated Jonagold apple orchard located at Halen, Belgium as a sport mutation of the Jonagold apple tree. Jonagold being a crossing of Golden Delicious with Jonathan, bred by New York State Agricultural experiment station, Geneva, N.Y. It was noted that a branch of a Jonagold tree in the orchard was unique and different in appearance from the entire block of Jonagold trees, and was bearing brown red apples about the beginning of September while the rest of the Jonagold fruit in the orchard was still green.

Observation of the spontaneous mutated branch over a period of three weeks indicated that the condition of the fruit remained stable although its color gradually became beautiful bright red. In comparison with the parent variety, the Excel has a much better color intensity over approximately 50% or more of the surface of the fruit with a solid bright red colored blush with scarcely visible very fine red stripes in it. The sport is already colored and picking-ripe ten days earlier than the fruit of the parent variety.

Cuttings were made from the mutated branch and the new variety was reproduced by grafting. Extended observation in Halen, Belgium has shown that the unique and distinguishing characteristics of the mutated branch and its fruit have remained consistent through its third generation descendants. The original mutated branch and its descendants have the very same characteristics and fruit color as described in this patent. We can say that the Excel is virus free and it is an improvement of the Jonagold variety with respect to its growth habit, color and productivity.

Various differences between the parent Jonagold apple variety and the new Excel apple variety are itemized in the following comparison table.

TABLE A

| | JONAGOLD | EXCEL |
|---|---|---|
| Fruit: | | |
| Over color: | orange-red striped striped blush: red group 45B changing to 45A when eating ripe. | red blush: red group 45A changing to 46A when eating ripe. Same color characteristics, although a much better color intensity over practically 50% and more of the surface of the fruit with a solid bright red colored blush with scarcely visible very fine red stripes in it. |
| Ground color: | | Degree of acidity of the apple is higher. keeps longer green. |
| Skin surface texture: | bumpy. | smooth. |
| | | 10 days earlier colored and ready to pick. |
| Stalk: | green | longer, thinner with a red/brown color. |
| Wood: | | |
| color: | brown | more red |
| pubescence: | few | clearly more. |
| lenticels: | small points. | fewer but bigger. |
| Dormant fruit buds on tips: | | |
| shape: | conical ovoid | conical |

THE DRAWNGS

The accompanying drawings illustrate my new Excel apple tree and the characteristics of its fruit taken at the time of fruit ripening for keeping.

FIG. 1 illustrates a plurality of Excel apples in various orientations.

FIG. 2 a closer view of Excel apples illustrating the color intensity of fruit and showing the red blush with scarcely visible very fine red stripes fading into very fine red stripes towards the green side, its long and thin red stalk also being seen.

DETAILED DESCRIPTION OF THE NEW VARIETY

Figure 1:
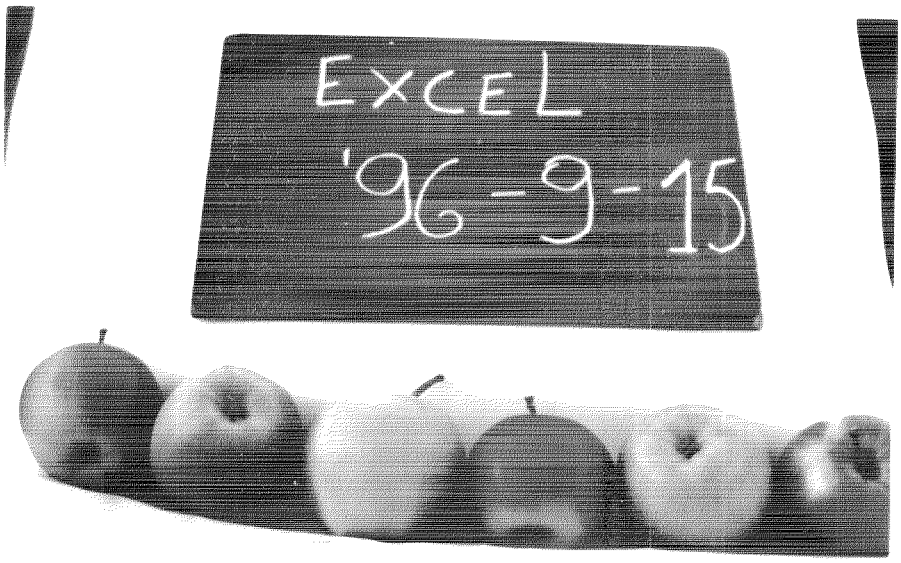
Figure 2:
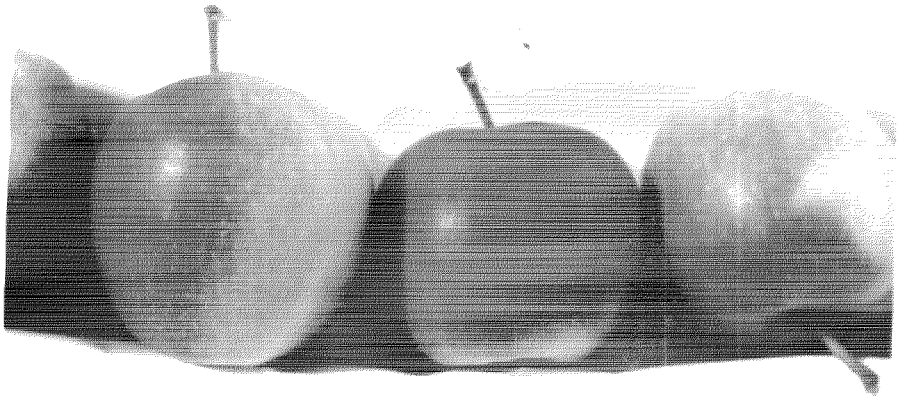
Figure 3:
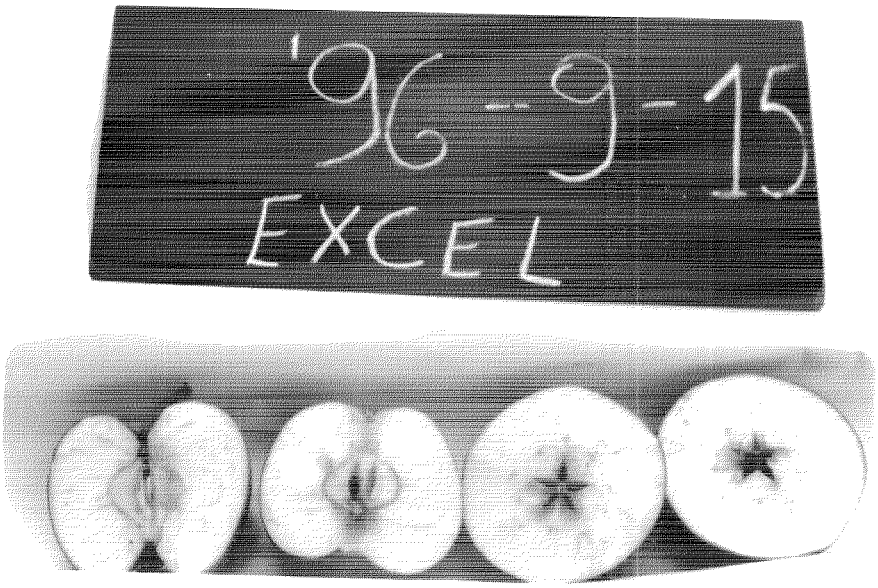
FIG. 3 is a view illustrating longitudinal and transverse sections taken through the fruit of the Excel variety.
Figure 4:
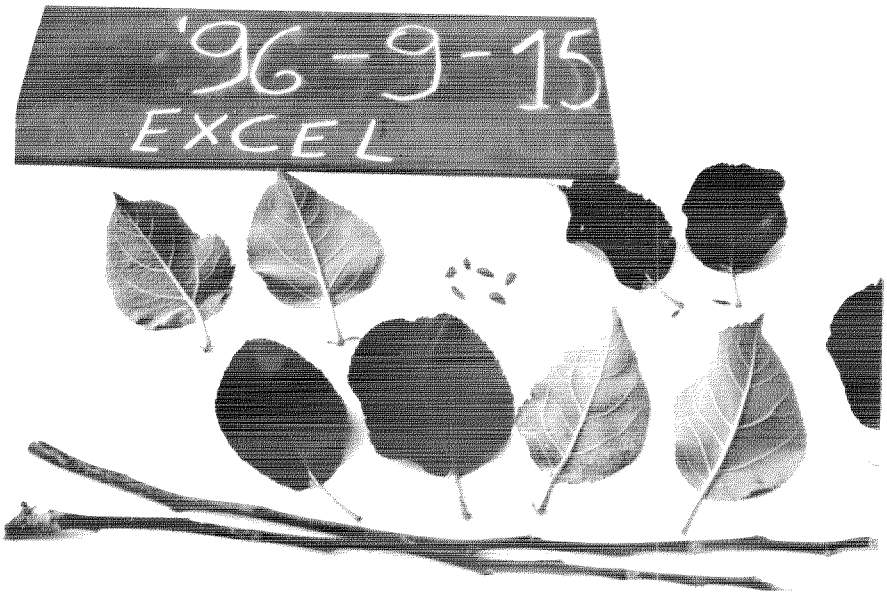
FIG. 4 is a view of the leaves and branches of the new Excel apple tree, along with the seeds of its fruit.
Figure 5:
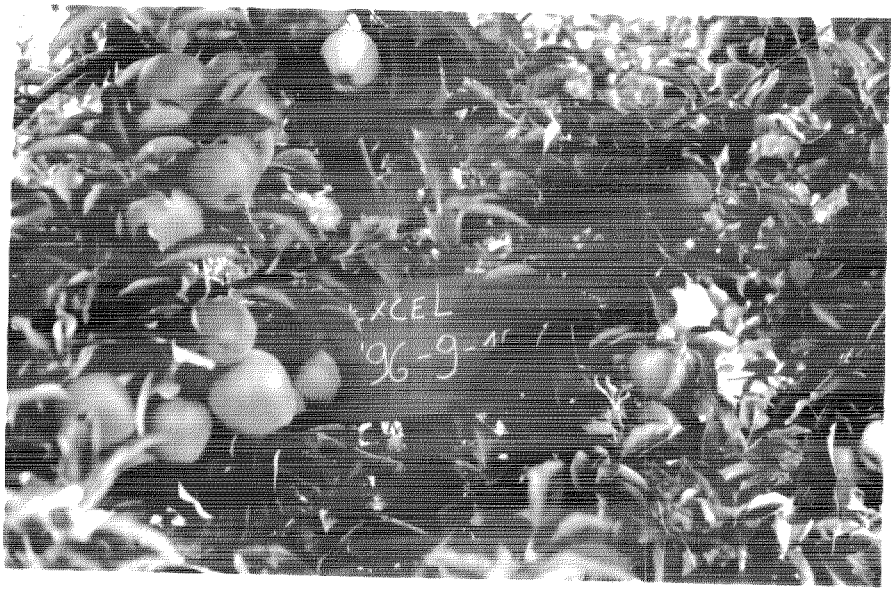
FIG. 5 shows the mutated, Excel branch and its fruit on its parent, fruit-bearing Jonagold tree.
Figure 6:
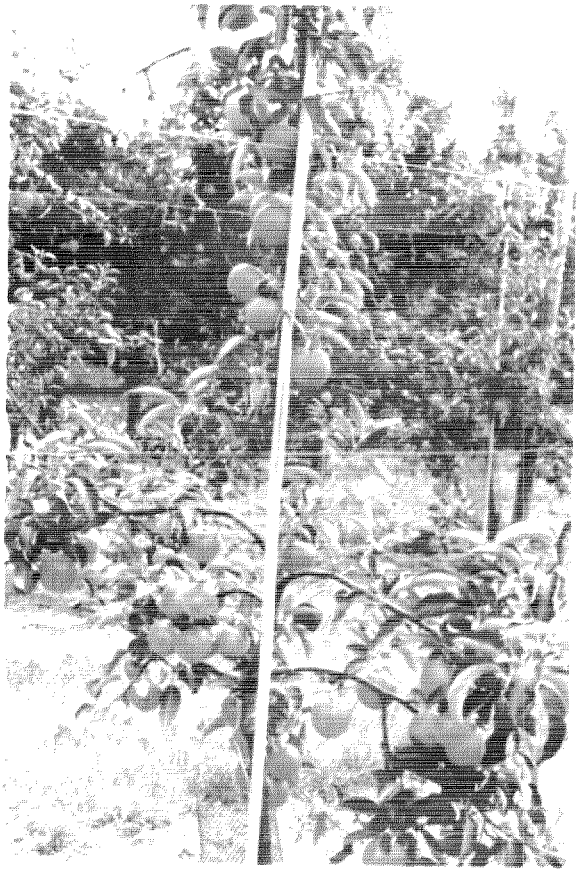
FIG. 6 illustrates the overall appearance and growth habit of an Excel apple tree.

The following is a detailed description of the new apple tree variety Excel as grown and observed in Halen, Belgium. Color references are made to The Royal Horticultural Colour Chart of London in association with the Flower Council of Leiden — Holland (1986), except where general color terms of ordinary dictionary significance are used.

Parentage: A sport mutation of the apple tree variety Jonagold.
Propagation: Asexually by budding and grafting.

The tree

Form: Medium size.
Habit of growth: Generally rapid, very productive, regular bearer.
Vigor (based on height and spread): Medium.
Trunk: Medium stocky, smooth, medium strong.
Branches: Drooping.
Density of head: Medium.
Predominance of bearing: On spurs (also tips).
Dormant one-year-old shoot (on October 14th):
*Thickness.*—Medium.
*Pubescence.*—Much; round about the shoot.
*Internode.*—From 0.06 cm to 4.8 cm (average of 2.69 cm).
*Number of lenticels.*—Few though present.
*Size of lenticels.*—Small; maximum 1.5 mm long; generally round points.
*Wood bud.*—Pubescence (on upper half of shoot): moderate.
*Form.*—Relatively straight.
*Color of wood.*—upper side: with pubescence darker reddish than greyed group 201A; without pubescence between brown group 200B and greyed-purple group 187A; Underside: with pubescence greyed-green group 197A; without pubescence darker brownish than yellow-green group 152A.
Dormant fruit buds (on October 14th).
*Shape.*—Conical.
*Apex.*—pointed.
*Pubescence.*—Moderate to much.
*Size.*—Medium.
*Length.*—From 3.79 to 7.00 mm (average of 5.29 mm).
*Width.*—From 3.29 to 5.00 mm (average of 4.03 mm).
Leaves (on October 14th):
*General pose.*—Outwards.
*L/B ratio.*—Medium.
*Margin.*—83% serrate of which 48% is serrate, 13% is sharp serrate, 9% is half serrate-half biserrate, 13% is biserrate and 17% is crenate and bicrenate.
*Size.*—Oval. Length: from 7.4 to 12.3 cm (average of 9.87 cm). Width: from 4.5 to 8.1 cm (average of 6.51 cm).
*Apex.*—Acuminate.
*Base.*—Obtuse.
*Color.*—Yellow-green group. Upper side: 147A. Under side 148A.
*Leave blade.*—With a very strong glossiness of upper side and a moderate to much pubescence on underside.
*Petiole.*—Long; length: from 1.7 to 3.4 cm (average of 2.37 cm), width measured in the middle: from 0.15 to 0.25 cm (average of 0.21 cm).
*Stipules.*—L/B ratio: much longer than broad; average length of 1.38 cm; average width of 0.20 cm.
Flowers:
*Time of beginning of flowering.*—Medium.
*Time of full flower.*—Medium.
*Shape.*—Moderately cupped.
*Size (diameter flower with petals pressed into horizontal positions).*—Medium.
*Petals.*—L/B ratio: longer than broad. Relation of margins: free.
*Sepal.*—Color: green with light brown-red tips.
*Styles.*—Length in relation to stamens: equal. Point of fusion: away from base.
*Pedicel.*—Long and red colored.

The fruit

Dates of first and last pickings: Approximately 15 September and 15 October, respectively; depending upon the year.
Time of fruit ripening for picking: Medium-late.
Time of fruit ripening for eating: Medium-late.
Size: Medium to large fruit.
General shape: Round. Vertical diameter of approximately 6.71 cm. Horizontal diameter of approximately 7.68 cm.
Symmetry: Asymmetric.
Ribbing: Present. Prominence of ribbing: Prominent.
Crowning at distal end: Present. Degree: weak to medim.
Aperture of eye: Half open.
*Size of eye.*—Large.
Sepals (visual:
*Length.*—Medium.
*Pose.*—Erect-convergent.
*Basis.*—Free.
Depth of eye basin: Deep 1.8 cm.
*Width of eye basin.*—Broad 2.33 cm.
*Ribbing of basin.*—Present.
Degree of ribbing: Medium to strong.
Stalk:
*Protrusion.*—Much beyond cavity.
*Thickness.*—Medium, 2.51 mm.
*Length.*—Long, 3.1 cm.
*Cavity depth of stalk.*—Deep, 1.61 cm.
*Width of stalk cavity.*—Medium 2.43 cm.
*Color.*—Red/brown.
Skin:
*Surface texture.*—Smooth.
*Bloom of skin.*—Absent.
*Greasiness of skin.*—Absent to weak.
*Cracking tendency of skin.*—Absent.
Thickness of skin: Medium.
*Shininess.*—Shiny.
Ground color of skin: Green-yellow; yellow-green group 150A.
Over color of skin: Red blush: red group 45A changing to 46A when eating ripe.
*Amont of over color.*—Practically 50% and more of the surface of the fruit.

Form: Solid bright red colored blush with scarcely visible very fine red stripes in it, fading into very fine red stripes towards the green side.

Russet: Present.

*Amount of russet: Moderate.*

Position of russet: Around stalk cavity.

*Color of russet.*—Buff.

*Lenticels.*—Size: medium.

*Number.*—Medium.

Flesh:

*Browning of the flesh (one hour after being cut, with stainless steel knife).*—Medium.

*Firmness.*—Firm. (measurement with penetrometer: 7.5).

*Color of the flesh.*—Yellow group 2D.

*Texture.*—Medium.

Juiciness: Juicy.

*Acidity.*—Medium.

*Sweetness.*—Medium.

Seeds:

*Length.*—0.83 cm.

*Breadth.*—0.33 cm.

*Form.*—Acuminate.

*Color.*—Greyed-orange group 165A.

Fruit in cross section section:

*Cavity beneath eye.*—V/U shaped.

*position of stamens.*—Basal.

*Shape of core.*—Symmetric.

*Distinctness of core-line (median through locules).*—Weak to medium.

Aperture of cells: Open, medium.

Other characteristics

Use: Particularly well-suited as a dessert fruit; juices and usable for culinary purposes as well.

Keeping quality:

*Natural conditions.*—Good.

*Refrigerated conditions.*—Keeps very well; depending on the ripeness of the fruit, it can be stored over 10 months.

Resistance to insects and diseases: No unusual susceptibility or resistance noted.

I claim:

1. The new and distinct variety of apple tree named Excel as described and illustrated, and which is particularly characterized over its parent variety by its much better color intensity over 50% or more of the surface of the fruit with a solid bright red colored blush with scarcely visible very fine red stripes in it and a smoother texture of the skin surface; by the ground color of its fruit keeping green longer; by the higher acidity in its fruit and a longer and thinner brown/red stalk; by the earlier ripening and picking dates of its fruit; by the tree's distinctly dormant fruit buds on tips which have a conical shape; and by its dark brown-red wood with clearly more pubescence and fewer but bigger lenticels than its parent variety.

* * * * *